(12) United States Patent
Samproni et al.

(10) Patent No.: US 11,549,936 B2
(45) Date of Patent: Jan. 10, 2023

(54) COMPOSITIONS COMPRISING STABILIZED OXYGEN AND METHODS OF FORMING THE SAME

(71) Applicant: Siemens Healthcare Diagnostics Inc., Tarrytown, NY (US)

(72) Inventors: Jennifer Samproni, Braintree, MA (US); Kevin Horan, Raynham, MA (US); Murli Narayan, Norfolk, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 236 days.

(21) Appl. No.: 16/769,395

(22) PCT Filed: Dec. 19, 2018

(86) PCT No.: PCT/US2018/066398
§ 371 (c)(1),
(2) Date: Jun. 3, 2020

(87) PCT Pub. No.: WO2019/126266
PCT Pub. Date: Jun. 27, 2019

(65) Prior Publication Data
US 2021/0405024 A1    Dec. 30, 2021

Related U.S. Application Data

(60) Provisional application No. 62/608,677, filed on Dec. 21, 2017.

(51) Int. Cl.
| | | |
|---|---|---|
| *G01N 33/49* | (2006.01) | |
| *G01N 27/327* | (2006.01) | |
| *G01N 33/66* | (2006.01) | |
| *G01N 33/68* | (2006.01) | |
| *A61K 47/18* | (2017.01) | |
| *A61K 47/26* | (2006.01) | |

(52) U.S. Cl.
CPC ......... *G01N 33/4925* (2013.01); *A61K 47/18* (2013.01); *A61K 47/26* (2013.01); *G01N 27/3274* (2013.01); *G01N 33/66* (2013.01); *G01N 33/68* (2013.01); *G01N 2496/70* (2013.01); *Y10T 436/102499* (2015.01); *Y10T 436/2525* (2015.01)

(58) Field of Classification Search
CPC ........ A61K 47/18; A61K 47/08; A61K 47/26; A61K 9/08; G01N 27/3274; G01N 33/49; G01N 33/4925; G01N 33/68; G01N 33/66; Y10T 436/10; Y10T 436/102499; Y10T 436/104998; Y10T 436/143333; Y10T 436/144444; Y10T 436/20; Y10T 436/207497; Y10T 436/209163; Y10T 436/2525
USPC ........... 436/8, 11, 14, 63, 68, 86, 89, 94, 95, 436/127, 136, 138, 176
See application file for complete search history.

(56) References Cited

U.S. PATENT DOCUMENTS

| | | | |
|---|---|---|---|
| 4,853,091 A | | 8/1989 | Mund et al. |
| 4,917,685 A | | 4/1990 | Viswanathan et al. |
| 5,780,302 A | * | 7/1998 | Conlon ................. B32B 15/085 436/68 |
| 6,066,249 A | * | 5/2000 | Manzoni ................ G01N 33/96 204/415 |
| 2004/0137633 A1 | | 7/2004 | Shin et al. |
| 2005/0203217 A1 | | 9/2005 | Pomrink |
| 2016/0025754 A1 | * | 1/2016 | Uretsky ................ G01N 33/96 436/8 |
| 2019/0298653 A1 | * | 10/2019 | Yamanouchi ........... A61K 9/08 |

FOREIGN PATENT DOCUMENTS

| | | |
|---|---|---|
| EP | 0689050 A1 | 12/1995 |
| JP | S60093952 A | 5/1985 |
| JP | S63105072 U | 7/1988 |
| JP | 2005534031 A | 11/2005 |
| WO | 9716309 A1 | 5/1997 |
| WO | 2004011931 A1 | 2/2004 |
| WO | 2014159816 A1 | 10/2014 |
| WO | 2017195852 A1 | 11/2017 |

OTHER PUBLICATIONS

International Search Report and Written Opinion of International Application No. PCT/US2018/066398 dated Mar. 15, 2019.
European Search Repod and Search Opinion of European Application No. 18891637.3 dated Aug. 21, 2020.
Gkogkolou et al., "Advanced Glycation End Products", 2012, Dermato-Endocrinology, Landes Bioscience 4:3, pp. 259-270.

* cited by examiner

*Primary Examiner* — Maureen Wallenhorst

(57) ABSTRACT

Disclosed herein are compositions that include oxygen, a sugar or sugar alcohol, and an amino acid, wherein the amino acid is present in an amount sufficient to stabilize the oxygen. Also provided are aqueous diagnostic quality controls or calibration reagents and methods of stabilizing oxygen in a liquid solution.

17 Claims, 2 Drawing Sheets

COMPOSITIONS COMPRISING STABILIZED OXYGEN AND METHODS OF FORMING THE SAME

The subject application claims benefit under 35 USC § 119(e) of U.S. provisional Application No. 62/608,677, filed Dec. 21, 2017. The entire contents of the above-referenced patent application are hereby expressly incorporated herein by reference.

FIELD OF THE INVENTION

Disclosed herein are compositions comprising stabilized oxygen and methods of forming the same.

BACKGROUND OF THE INVENTION

Aqueous diagnostic quality controls and calibration reagents generally must be stored at 2-8° C. due to the instability of oxygen (pO2) at room temperature. Users may require assays to be performed where refrigeration is not available nearby making expansion of the storage temperature range to 2-30° C. preferable. Thus, storage at 2-8° C. is often times not sufficient for storing diagnostic quality controls and calibration reagents.

SUMMARY OF THE INVENTION

Disclosed herein are compositions comprising oxygen, a sugar or sugar alcohol, and an amino acid, wherein the amino acid is present in an amount sufficient to stabilize the oxygen.

Aqueous diagnostic quality controls or calibration reagents comprising any of the disclosed compositions are also provided.

Further provided are methods of stabilizing oxygen in a liquid solution, the methods comprising adding a stabilizing amount of an amino acid to the liquid solution, wherein the liquid solution contains oxygen and a sugar or sugar alcohol.

BRIEF DESCRIPTION OF THE DRAWINGS

The summary, as well as the following detailed description, is further understood when read in conjunction with the appended drawings. For the purpose of illustrating the disclosed compositions, reagents, and methods there are shown in the drawings exemplary embodiments of the compositions, reagents, and methods; however, the compositions, reagents, and methods are not limited to the specific embodiments disclosed. In the drawings.

DETAILED DESCRIPTION OF ILLUSTRATIVE EMBODIMENTS

Figure 1:
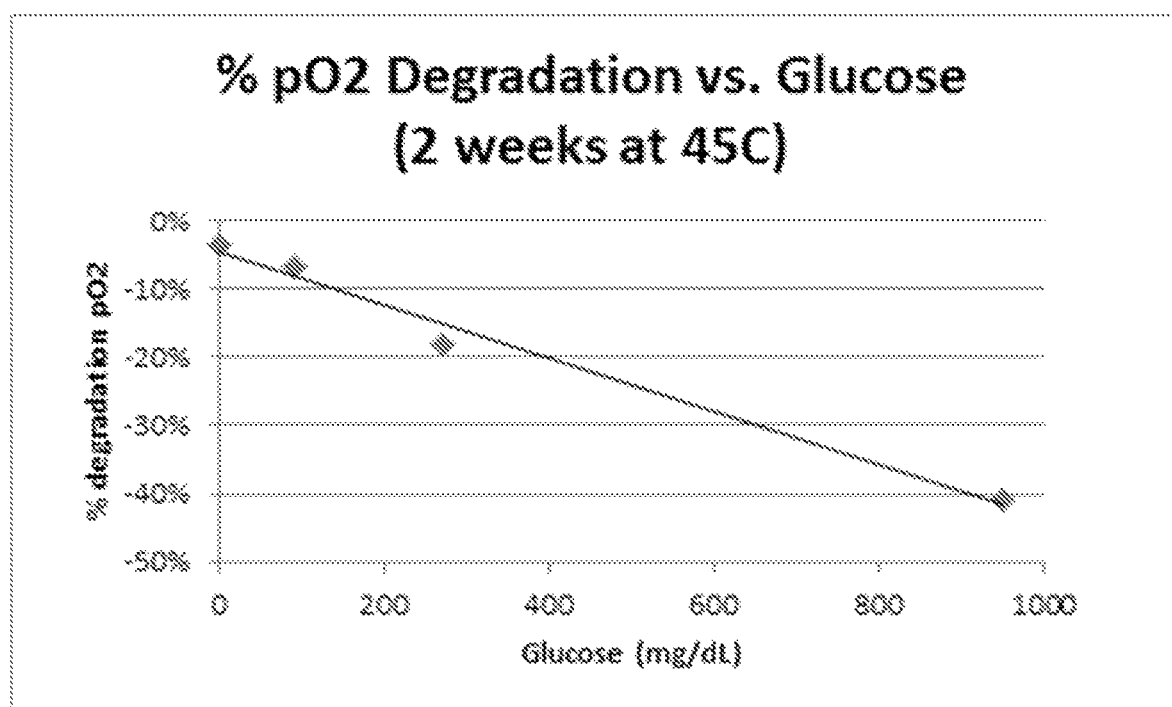
FIG. 1 illustrates the percent (%) pO2 degradation vs. glucose concentration in solutions stored for 2 weeks at 45° C.

The disclosed compositions, reagents, and methods may be understood more readily by reference to the following detailed description taken in connection with the accompanying figures, which form a part of this disclosure. It is to be understood that the disclosed compositions, reagents, and methods are not limited to the specific compositions, reagents, and methods described and/or shown herein, and that the terminology used herein is for the purpose of describing particular embodiments by way of example only and is not intended to be limiting of the claimed compositions, reagents, and methods.

Unless specifically stated otherwise, any description as to a possible mechanism or mode of action or reason for improvement is meant to be illustrative only, and the disclosed compositions, reagents, and methods are not to be constrained by the correctness or incorrectness of any such suggested mechanism or mode of action or reason for improvement.

Throughout this text, the descriptions refer to compositions comprising stabilized oxygen and methods of stabilizing oxygen in a liquid solution. Where the disclosure describes or claims a feature or embodiment associated with the compositions, such a feature or embodiment is equally applicable to the disclosed methods. Likewise, where the disclosure describes or claims a feature or embodiment associated with the disclosed methods, such a feature or embodiment is equally applicable to the compositions.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed compositions, reagents, and methods which are, for clarity, described herein in the context of separate embodiments, may also be provided in combination in a single embodiment. Conversely, various features of the disclosed compositions, reagents, and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

In solutions containing oxygen and various sugars and sugar alcohols, such as glucose, the sugars/sugar alcohols have a tendency to destabilize the oxygen through a chemical reaction. The disclosed compositions address this problem through the addition of an oxygen-stabilizing amount of an amino acid, which prevents the sugar- or sugar alcohol-induced destabilization of oxygen. The disclosed compositions comprise oxygen, a sugar or sugar alcohol, and an amino acid, wherein the amino acid is present in an amount sufficient to stabilize the oxygen.

Suitable sugars and sugar alcohols include, but are not limited to, glucose, maltose, lactose, maltulose, iso-maltulose lactulose, or combinations thereof. In some embodiments, the sugar is glucose.

The disclosed compositions contain one or more amino acids that inhibit the chemical reaction between the sugar/sugar alcohol and oxygen. Suitable amino acids include, for example, those containing a free amino, imino, or guanidino side chain. The amino acid can be D or L forms of ornithine, taurine, threonine, citrulline, histidine, lysine, arginine, tryptophan, aminoguanidine derivatives, amphotericin, or any combination thereof. In some embodiments, the amino acid is ornithine.

The amino acid is present in an amount sufficient to increase the stabilization of the oxygen relative to a control composition, wherein the control composition comprises the oxygen and the sugar or sugar alcohol but not the amino acid. The increased stabilization of the oxygen relative to the control composition can take place at any temperature. For example, the amino acid can be present in an amount sufficient to increase the stabilization of the oxygen for extended storage at 4° C., 37° C., room temperature, or any temperature suitable for storage of the composition. In some embodiments, the amino acid is present in an amount sufficient to stabilize the oxygen for extended room temperature storage relative to a control composition, wherein the control composition comprises the oxygen and the sugar or sugar alcohol but not the amino acid. The extended storage can be for one month, two months, three months, four months, five months, six months, seven months, eight months, nine months, ten months, eleven months, one year, or greater than one year. In some embodiments, the extended room temperature storage is for six months to a year.

In some embodiments, the pO2 loss is less than about 10 mmHg over a 24 week storage period at room temperature. The pO2 loss can be about 1 mmHg, 2 mmHg, 3 mmHg, 4 mmHg, 5 mmHg, 6 mmHg, 7 mmHg, 8 mmHg, 9 mmHg, or 10 mmHg over a 24 week storage period at room temperature. In some embodiments, the pO2 loss is reduced by 10%, 20%, 30%, 40%, 50%, 60%, 70%, 80% or 90% relative to the control composition.

Suitable concentrations of the amino acid include from about 0.1 mmol/l to about 20 mmol/l, from about 0.5 mmol/l to about 15 mmol/l, from about 1 mmol/l to about 10 mmol/l, or from about 1.5 mmol/l to about 5 mmol/l. In some embodiments, the composition comprises from about 0.5 mmol/l to about 11 mmol/l of the amino acid.

The composition can comprise from about 10 mmHg to about 1000 mmHg, from about 15 mmHg to about 850 mmHg, from about 20 mmHg to about 700 mmHg, from about 50 mmHg to about 500 mmHg, or from about 100 mmHg to about 250 mmHg of oxygen. In some embodiments, the composition comprises from about 25 mmHg to about 650 mmHg of oxygen.

The composition can comprise from about 5 mg/dl to about 1000 mg/dl, from about 15 mg/dl to about 900 mg/dl, from about 20 mg/dl to about 800 mg/dl, or from about 50 mg/dl to about 500 mg/dl of glucose. In some embodiments, the composition comprises from about 27 mg/dl to about 750 mg/dl of glucose.

In addition to the oxygen, sugar or sugar alcohol, and amino acids, the composition can further comprise urea, measured as Blood Urea Nitrogen (BUN), salts, buffers, preservatives, and/or surfactants. The concentration of BUN can be from about 1 mg/dl to about 200 mg/dl, from about 2 mg/dl to about 175 mg/dl, from about 3 mg/dl to about 150 mg/dl, from about 4 mg/dl to about 100 mg/dl, or from about 5 mg/dl to about 50 mg/dl. In some embodiments, the composition comprises from about 4.5 mg/dl to about 90 mg/dl of BUN. Suitable salts include sodium, chloride, potassium, calcium, magnesium, or any combination thereof. Suitable buffers include phosphate, MES, MOPS, MOPSO, HEPES, and TRIS. Suitable surfactants include Triton, BRIJ, and Surfynol. Suitable preservatives include MIT, Cl-MIT, and azides.

The composition can have a pH of from about 6 to about 9, from about 6.2 to about 8.5, or from about 6.4 to about 8. In some embodiments, the composition can have a pH of from about 6.6 to about 7.7.

The disclosed composition can be disposed in a closed system. Suitable closed systems include, for example, a flexible pouch, a ampoule, a bottle, a tube, a cartridge, and the like. The closed system can be glass or polypropylene.

Also provided herein are aqueous diagnostic quality controls or calibration reagents comprising any of the compositions disclosed herein.

The disclosed aqueous diagnostic quality controls and calibration reagents can be adapted to calibrate oxygen sensors, glucose sensors, or both oxygen sensors and glucose sensors in a analytical instrument. The disclosed aqueous diagnostic quality controls and calibration reagents can used in various medical diagnostic applications including, but not limited to, the detection/diagnosis of disease states (such as hyperglycermia/hypoglycemia) and metabolic states (oxygen content), as well as in food or beverage testing, agriculture, and pharmaceutical development or testing.

Also provided are methods of stabilizing oxygen in a liquid solution, the method comprising adding a stabilizing amount of an amino acid to the liquid solution, wherein the liquid solution contains oxygen and a sugar or sugar alcohol.

The amino acid is one that inhibits the chemical reaction between the sugar/sugar alcohol and oxygen. Suitable amino acids include, for example, those containing a free amino, imino, or guanidino side chain. The amino acid can be D or L forms of ornithine, taurine, threonine, citrulline, histidine, lysine, arginine, tryptophan, aminoguanidine derivatives, amphotericin, or any combination thereof. In some embodiments, the amino acid is ornithine.

The stabilizing amount of the amino acid is an amount sufficient to increase the stabilization of the oxygen relative to a control composition, wherein the control composition comprises the oxygen and the sugar or sugar alcohol but not the amino acid. The increased stabilization of the oxygen relative to the control composition can take place at any temperature. For example, the methods can comprise adding the amino acid in an amount sufficient to increase the stabilization of the oxygen for extended storage at 4° C., 37°

C., room temperature, or any temperature suitable for storage of the liquid solution. In some embodiments, the method comprises adding an amount of the amino acid sufficient to stabilize the oxygen for extended room temperature storage relative to a control composition, wherein the control composition comprises the oxygen and the sugar or sugar alcohol but not the amino acid. The extended storage can be for one month, two months, three months, four months, five months, six months, seven months, eight months, nine months, ten months, eleven months, one year, or greater than one year. In some embodiments, the extended room temperature storage is for six months to a year. Suitable concentrations of the amino acid include from about 0.1 mmol/l to about 20 mmol/l, from about 0.5 mmol/l to about 15 mmol/l, from about 1 mmol/l to about 10 mmol/l, or from about 1.5 mmol/l to about 5 mmol/l. In some embodiments, the method comprises adding from about 0.5 mmol/l to about 11 mmol/l of the amino acid to the liquid solution.

In some embodiments, the pO2 loss is less than about 10 mmHg over a 24 week storage period at room temperature. The pO2 loss can be about 1 mmHg, 2 mmHg, 3 mmHg, 4 mmHg, 5 mmHg, 6 mmHg, 7 mmHg, 8 mmHg, 9 mmHg, or 10 mmHg over a 24 week storage period at room temperature. In some embodiments, the pO2 loss is reduced by 10%, 20%, 30%, 40%, 50%, 60%, 70%, 80% or 90% relative to the control composition.

The liquid solution can comprise from about 10 mmHg to about 1000 mmHg, from about 15 mmHg to about 850 mmHg, from about 20 mmHg to about 700 mmHg, from about 50 mmHg to about 500 mmHg, or from about 100 mmHg to about 250 mmHg of oxygen. In some embodiments, the liquid solution comprises from about 25 mmHg to about 650 mmHg of oxygen.

The liquid solution can comprise from about 5 mg/dl to about 1000 mg/dl, from about 15 mg/dl to about 900 mg/dl, from about 20 mg/dl to about 800 mg/dl, or from about 50 mg/dl to about 500 mg/dl of glucose. In some embodiments, the liquid solution comprises from about 27 mg/dl to about 750 mg/dl of glucose.

In some embodiments, the liquid solution is an aqueous diagnostic quality control or calibration reagent for use with a diagnostic sensor. Diagnostic sensors include, but are not limited to, sensors for the sugar or sugar alcohol and/or oxygen. In some embodiments, the sensor for the sugar or sugar alcohol is a glucose sensor.

Examples

The following examples are provided to further describe some of the embodiments disclosed herein. The examples are intended to illustrate, not to limit, the disclosed embodiments.

In solutions containing oxygen and various sugars and sugar alcohols, such as glucose, the sugars/sugar alcohols have a tendency to destabilize the oxygen through a chemical reaction. This is exemplified in FIG. 1, which shows the loss of oxygen (% degradation of pO2) with increasing concentrations of glucose when stored for 2 weeks at 45° C. As shown in FIG. 1, the addition of glucose causes a loss of pO2, which is increased with increasing concentrations of glucose.

Figure 2:
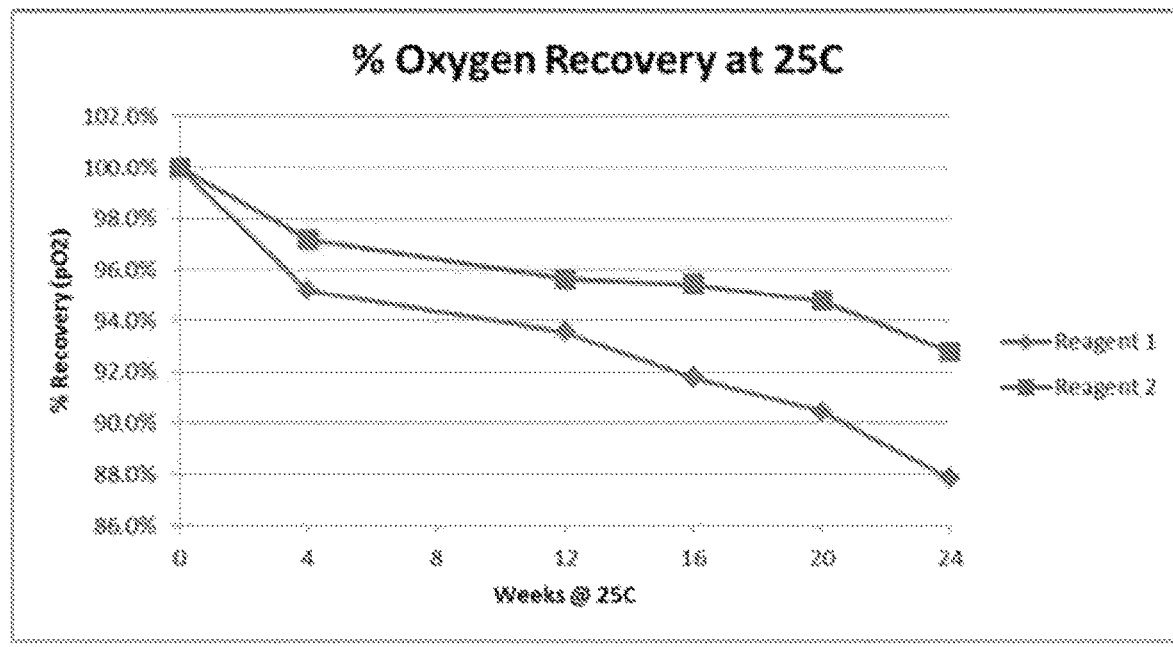
FIG. 2 illustrates the percent (%) oxygen recovery in amino acid containing solutions stored at 25° C. for 12 weeks as compared to time zero (baseline).

The ability of the exemplary amino acids arginine and ornithine to stabilize oxygen at 25° C. was tested. Glucose containing solutions comprising arginine or ornithine (Table 1) were sparged with oxygen and then sealed within a closed system. The % oxygen recovery was analyzed in samples stored at 25° C. for 12 weeks and compared to time zero (baseline). As shown in Table 1 and FIG. 2, 93.6% and 95.7% of the oxygen was recovered from samples containing arginine or ornithine, respectively, stored at 25° C. for 12 weeks as compared to time zero.

TABLE 1

Oxygen recovery after 12 weeks at 25° C.

| Sample Name | Amino Acid | Sugar | % Oxygen Recovery after 12 weeks at 25° C. compared to Baseline (Time = 0) |
|---|---|---|---|
| Reagent 1 | 1.94 g/L arginine | 0.5 g/L glucose | 93.6% |
| Reagent 2 | 2.41 g/L ornithine | 0.5 g/L glucose | 95.7% |

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of stabilizing oxygen in a liquid solution an aqueous diagnostic quality control or calibration reagent adapted to calibrate an oxygen sensor and/or a glucose sensor of an analytical instrument, the method comprising:
   adding a stabilizing amount of an amino acid to a liquid solution, wherein the liquid solution contains oxygen and a sugar or sugar alcohol selected from the group consisting of glucose, maltose, lactose, maltulose, isomaltulose, lactulose, or any combination thereof, and wherein the amino acid is selected from the group consisting of ornithine, arginine, or a combination thereof; and
   sealing the amino acid-containing liquid solution in a closed system to form the aqueous diagnostic quality control or calibration reagent;
   wherein the stabilizing amount of the amino acid inhibits a chemical reaction between the sugar or sugar alcohol and the oxygen and stabilizes the oxygen (pO$_2$) relative to a control composition which comprises the oxygen and the sugar or sugar alcohol but not the amino acid for an extended room temperature storage period, wherein the extended room temperature storage period is at least about two months, and wherein oxygen loss in the amino acid-containing liquid solution is less than about 10% of an original oxygen concentration over the extended room temperature storage period.

2. The method of claim 1, wherein the amino acid is ornithine.

3. The method of claim 1, wherein the liquid solution contains from about 0.5 mmol/l to about 11 mmol/l of the amino acid.

4. The method of claim 1, wherein the liquid solution contains from about 25 mmHg to about 650 mmHg of oxygen.

5. The method of claim 1, wherein the liquid solution contains from about 27 mg/dl to about 750 mg/dl of glucose.

6. The method of claim 1, wherein the amino acid is arginine.

7. The method of claim 1, wherein the liquid solution does not contain urea.

8. An aqueous diagnostic quality control or calibration reagent adapted to calibrate an oxygen sensor and/or a glucose sensor of an analytical instrument, wherein the aqueous diagnostic quality control or calibration reagent is sealed within a closed system, and wherein the aqueous diagnostic quality control or calibration reagent comprises:
oxygen;
a sugar or sugar alcohol selected from the group consisting of glucose, maltose, lactose, maltulose, iso-maltulose, lactulose, or any combination thereof; and
an amino acid selected from the group consisting of ornithine, arginine, or a combination thereof; and
wherein the amino acid is present in an amount sufficient to inhibit a chemical reaction between the sugar or sugar alcohol and the oxygen ($pO_2$) and thereby stabilize the oxygen relative to a control composition which comprises the oxygen and the sugar or sugar alcohol but not the amino acid for an extended room temperature storage period, wherein the extended room temperature storage period is at least about two months, and wherein oxygen loss in the aqueous diagnostic quality control or calibration reagent is less than about 10% of an original oxygen concentration over the extended room temperature storage period.

9. The aqueous diagnostic quality control or calibration reagent of claim 8, wherein the amino acid is ornithine.

10. The aqueous diagnostic quality control or calibration reagent of claim 8, wherein the amino acid is arginine.

11. The aqueous diagnostic quality control or calibration reagent of claim 8, wherein the aqueous diagnostic quality control or calibration reagent does not contain urea.

12. The aqueous diagnostic quality control or calibration reagent of claim 8, wherein the amino acid is present at a concentration in a range of from about 0.5 mmol/l to about 11 mmol/l.

13. The aqueous diagnostic quality control or calibration reagent of claim 8, wherein oxygen is present at a concentration in a range of from about 25 mmHg to about 650 mmHg.

14. The aqueous diagnostic quality control or calibration reagent of claim 8, further comprising glucose at a concentration in a range of from about 27 mg/dl to about 750 mg/dl.

15. The aqueous diagnostic quality control or calibration reagent of claim 8, further comprising Blood Urea Nitrogen (BUN) at a concentration in a range of from about 4.5 mg/dl to about 200 mg/dl.

16. The aqueous diagnostic quality control or calibration reagent of claim 8, further comprising sodium, chloride, potassium, calcium, magnesium, or any combination thereof.

17. The aqueous diagnostic quality control or calibration reagent of claim 8, wherein the reagent has a pH of from about 6.6 to about 7.7.

* * * * *